United States Patent [19]
Kramer et al.
[11] 4,124,369
[45] Nov. 7, 1978

[54] COMBATING FUNGI AND CONTROLLING PLANT GROWTH WITH 1-AMIDO-1-AZOLYL-2-HYDROXY- OR -KETO-ALKANES

[75] Inventors: Wolfgang Krämer; Wilfried Draber; Karl H. Büchel, all of Wuppertal; Wilhelm Brandes, Cologne; Klaus Lürssen, Bergisch-Gladbach, all of Germany

[73] Assignee: Bayer Aktiengesellschaft, Leverkusen, Germany

[21] Appl. No.: 798,745

[22] Filed: May 19, 1977

[30] Foreign Application Priority Data

Jun. 1, 1976 [DE] Fed. Rep. of Germany ....... 2624529

[51] Int. Cl.$^2$ ........................ A01N 9/22; A61K 31/41; A61K 31/415; C07D 249/08

[52] U.S. Cl. ........................................... 71/76; 71/74; 71/77; 71/78; 71/92; 260/308 R; 260/308 A; 260/326 A; 260/556 A; 260/556 AR; 260/561 R; 424/232; 424/269; 424/273 R; 548/341

[58] Field of Search ........................ 260/308 R, 308 A; 548/341; 424/269, 232, 273; 71/92, 74, 76, 77, 78

[56] References Cited

U.S. PATENT DOCUMENTS 3,993,469 11/1976 Regel et al. .......................... 548/341

*Primary Examiner*—Alton D. Rollins
*Attorney, Agent, or Firm*—Burgess, Dinklage & Sprung

[57] ABSTRACT

1-Amido-1-azolyl-2-hydroxy- or -keto-alkanes of the formula

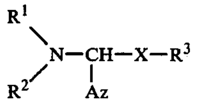

(I)

in which $R^1$ represents acyl or the grouping $R^4$—$SO_2$—, in which $R^4$ denotes alkyl or optionally substituted aryl,
$R^2$ represents hydrogen, or
$R^1$ and $R^2$ conjointly with the linking nitrogen atom represent an imide radical,
$R^3$ represents alkyl or optionally substituted aryl,
X represents a keto group or a CH(OH) grouping, and
Az represents an azole radical, and their physiologically tolerated salts which possess fungicidal and plant growth regulating properties.

9 Claims, No Drawings

COMBATING FUNGI AND CONTROLLING PLANT GROWTH WITH 1-AMIDO-1-AZOLYL-2-HYDROXY- OR -KETO-ALKANES

The present invention relates to and has for its objects the provision of particular new 1-amido-1-azolyl-2-hydroxy- or -keto-alkanes which possess fungicidal and plant growth regulating properties, active compositions in the form of mixtures of such compounds with solid and liquid dispersible carrier vehicles, and methods for producing such compounds and for using such compounds in a new way especially for combating pests, e.g. fungi, and for regulating plant growth with other and further objects becoming apparent from a study of the within specification and accompanying examples.

It has already been disclosed that certain trityl-1,2,4-triazoles, such as triphenyl-1,2,4-triazol-1-yl-methane, possess a good fungicidal activity (see German Offenlegungsschrift (German Published Specification) 1,795,249). However, their action is not always entirely satisfactory, especially when low amounts and low concentrations are used. Furthermore, it is known that a product based on fatty alcohols with 6, 8, 10 and 12 carbon atoms can be employed for regulating plant growth, especially for suppressing the growth of side shoots in tobacco (a commercial product of this type is described in Farm Chemicals Handbook 1975, Meister Publishing Company, Willoughby Ohio (U.S.A.), Pesticide Dictionary D 147). However, the action of this compound is not always entirely satisfactory, especially when low amounts and low concentrations are used.

The present invention now provides, as new compounds, the aminomethylazole derivatives of the general formula

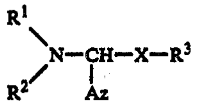

(I)

in which $R^1$ represents acyl or the grouping $R^4$—$SO_2$—, in which $R^4$ denotes alkyl or optionally substituted aryl, $R^2$ represents hydrogen, or $R^1$ and $R^2$ conjointly with the linking nitrogen atom represent an imide radical, $R^3$ represents alkyl or optionally substituted aryl, X represents a keto group or a CH(OH) grouping and Az represents an azole radical, and their physiologically tolerated salts.

Surprisingly, the active compounds according to the invention exhibit a substantially greater fungicidal action than triphenyl-1,2,4-triazol-1-yl-methane, known from the state of the art, and a better plant-growth-regulating action than a product based on fatty alcohols. The active compounds according to the invention thus represent a valuable enrichment of the art.

Preferably, $R^1$ denotes the grouping $R^4$—$SO_2$—, in which $R^4$ denotes alkyl with 1 to 4 carbon atoms or phenyl which is optionally monosubstituted or polysubstituted by halogen (especially fluorine, chlorine and bromine) or by alkyl with 1 or 2 carbon atoms, or $R^1$ represents acyl of the formula $R^5$—CO—, in which $R^5$ denotes straight-chain or branched alkyl with 1 to 4 carbon atoms, halogenoalkyl with up to 2 carbon atoms and up to 5 (especially up to 3) halogen atoms (preferably fluorine or chlorine), cycloalkyl with 5 to 7 (especially with 6) carbon atoms, which is optionally substituted by alkyl with 1 or 2 carbon atoms, or denotes aryl, aralkyl or aryloxyalkyl, each with 6 to 10 (especially 6) carbon atoms in the aryl part and the last two each having up to 4 carbon atoms in the alkyl part, which alkyl part is optionally substituted by halogen (especially chlorine) whereas the aryl part of these three radicals optionally carries one or more substituents selected from halogen (especially fluorine, chlorine and bromine), alkyl with 1 to 4 carbon atoms, halogenoalkyl with up to 2 carbon atoms and up to 5 (especially up to 3) halogen atoms (preferably fluorine or chlorine), alkoxy or alkylthio each with up to 2 carbon atoms, nitro, cyano, or phenyl or phenoxy, either of which is optionally substituted by halogen (especially chlorine), $R^2$ represents hydrogen, or $R^1$ and $R^2$, conjointly with the linking nitrogen atom, represent an imide radical (especially the phthalimide radical), $R^3$ represents straight-chain or branched alkyl with 1 to 4 carbon atoms or phenyl which is optionally substituted by halogen, (especially fluorine, chlorine and bromine) and/or by alkyl with 1 or 2 carbon atoms, and Az represents imidazol-1-yl, 1,2,4-triazol-1-yl, 1,2,4-triazol-4-yl and 1,2,3-triazol-1-yl.

Those compounds of the formula (I) in which X represents the CH(OH) grouping possess two asymmetrical carbon atoms; they can therefore exist in the erythro form and in the threo form. In both cases, they may be present as racemates.

The present invention also provides a process for the preparation of an aminomethylazole derivative of the formula (I) in which (a), when X is to represent the keto group, a halogenoamide-ketone of the general formula

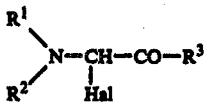

(II), in which $R^1$, $R^2$ and $R^3$ have the above-mentioned meanings and

Hal represents halogen, preferably chlorine or bromine, is reacted with an azole of the general formula Az — H (III), in which Az has the above-mentioned meaning, if appropriate in the presence of an acid-binding agent and/or of a diluent, or (b), when X is to represent the CH(OH) grouping, a keto-derivative of the general formula

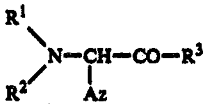

(XI), in which $R^1$, $R^2$, $R^3$ and Az have the above-mentioned meanings, obtainable according to process variant (a), is selectively reduced with a complex borohydride, if appropriate in the presence of a diluent. If required, the aminomethylazole derivative (I) obtained by either of the process variants (a) and (b) can then be converted into a physiologically tolerated salt thereof.

If 1-chloro-1-(p-chlorobenzamide)-3,3-dimethylbutan-2-one and 1,2,4-triazole are used as starting materials in process variant (b), the course of the reaction can be represented by the following equation:

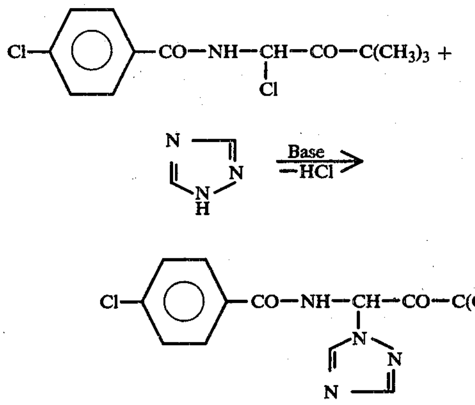

If 1-benzamido-3,3-dimethyl-1-(1,2,4-triazol-1-yl)-butan-2-one and sodium borohydride are used as starting materials in process variant (b), the course of the reaction can be represented by the following equation:

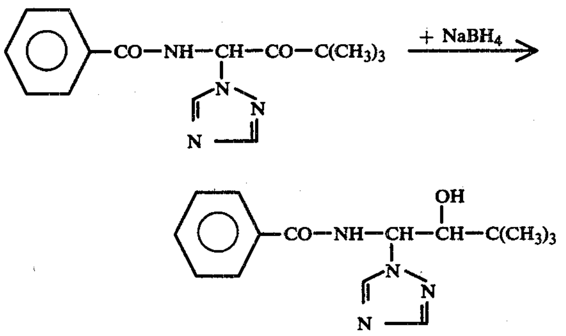

Halogenoamide-ketones, of the formula (II), which can be used according to the invention, have been described in Archiv Pharmazie 301, 867 (1968); Die Pharmazie 25, 522 (1970); Synthesis 1972, 380; Pharmaceutica Acta Helvetiae 48, 43 (1973). They can be prepared by ($\alpha$) reacting hydroxyamide-ketones of the general formula

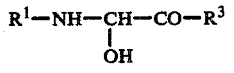 (IV), in which $R^1$ and $R^3$ have the above-mentioned meanings, with halogenating agents, for example phosphorus pentachloride, or thionyl chloride, in the presence of a diluent, such as, for example, carbon tetrachloride, at the boiling point of the solvent (see also the above-mentioned literature references and the preparative Examples given later in this text); or by ($\beta$) reacting amide derivatives of the general formula

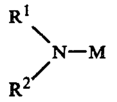 (V), in which $R^1$ and $R^2$ have the above-mentioned meanings and

M represents sodium or potassium, with a halogenoketone of the general formula $$Hal-CH_2-CO-R^3 \quad (VI),$$

in which $R^3$ has the above-mentioned meaning and

Hal represents halogen, preferably chlorine or bromine, in the presence of a diluent, for example acetone or dioxane, at temperatures between 0° and 60° C., and subsequently replacing the remaining active hydrogen atom by halogen in the usual manner (see also the preparative Examples); or by ($\gamma$) reacting halogen compounds of the general formula $$R^1-Hal \quad (VII),$$

in which $R^1$ has the above-mentioned meaning and

Hal represents halogen, preferably chlorine or bromine, with aminoketones of the formula $$H_2N-CH_2-CO-R^3 \quad (VIII),$$

in which $R^3$ has the above-mentioned meaning, in the presence of a diluent, for example carbon tetrachloride, at temperatures between 0° and 80° C., and subsequently replacing the remaining active hydrogen atom by halogen in the usual manner (see also the preparative examples).

Hydroxyamide-ketones of the formula (IV) have been described in the above-mentioned literature references. They can be prepared by reacting amide derivatives of the general formula $$R^1-NH_2 \quad (IX),$$

in which $R^1$ has the above-mentioned meaning, with glyoxyl derivatives of the general formula $$OCH-CO-R^3 \quad (X),$$

in which $R^3$ has the above-mentioned meaning in the presence of a solvent, for example benzene, at the boiling point of the solvent (see also the preparative examples).

The azoles of the formula (III) which can be used according to the invention are compounds generally known in organic chemistry.

Possible salts of the compounds of the formula (I) are salts with physiologically tolerated acids, especially the hydrogen halide acids, such as, for example, hydrobromic acid and, especially, hydrochloric acid, phosphoric acid, nitric acid, monofunctional and bifunctional carboxylic acids and hydroxycarboxylic acids, such as, for example, acetic acid, maleic acid, succinic acid, fumaric acid, citric acid, salicylic acid, sorbic acid, tartaric acid, and lactic acid, and 1,5-naphthalene-disulphonic acid.

The salts of the compounds of the formula (I) can be obtained in a simple manner in accordance with customary methods of forming salts, for example by dissolving the base in an ether, for example diethyl ether, and adding the acid, for example nitric acid, and can, using known methods, be isolated, for example by filtration, and be purified if appropriate.

Possible diluents for the reaction according to the invention, in accordance with process variant (a), are inert organic solvents, especially ketones, such as diethyl ketone and, especially, acetone and methyl ethyl ketone; nitriles, such as propionitrile and especially acetonitrile; alcohols, such as ethanol or isopropanol; ethers, such as tetrahydrofuran or dioxane; benzene; formamides, such as, in particular, dimethylformamide; and halogenated hydrocarbons.

The reaction according to process variant (a) is generally carried out in the presence of an acid-binding agent. All inorganic or organic acid-binding agents which can usually be employed may be added, such as alkali metal carbonates, for example sodium carbonate, potassium carbonate and sodium hydrogen carbonate, or such as lower tertiary alkylamines, cycloalkylamines or aralkylamines, for example triethylamine, N,N-dimethyl-benzylamine and dicyclohexylamine, or such as pyridine and diazabicyclooctane.

In process variant (a), the reaction temperatures can be varied within a fairly wide range. In general, the reaction is carried out at from 20° to 150° C., preferably at from 20° to 100° C.

In carrying out process variant (a), preferably 1 to 3 moles of azole and 1 to 2 moles of acid-binding agent are employed per mole of the compound of the formula (II). To isolate the compounds of the formula (I), the solvent is distilled off and the residue is taken up in a mixture of an organic solvent and water, and the organic phase is dried over sodium sulphate and freed from the solvent in vacuo. The residue is worked up in accordance with generally customary methods and is purified, if appropriate, by distillation or recrystallization.

If process variant (b) is followed, possible diluents for the reaction according to the invention are polar organic solvents, especially alcohols, such as methanol, ethanol, butanol and isopropanol, and ethers, such as diethyl ether or tetrahydrofuran. The reaction is in general carried out at 0° to 30° C., preferably at 0° to 20° C. For this reaction, about 1 mole of a borohydride, such as sodium borohydride or lithium borohydride, is employed per mole of the compound of the formula (XI). To isolate the compound of the formula (I), the residue is taken up in, for example, dilute hydrochloric acid, then rendered alkaline and extracted with an organic solvent; alternatively, it is mixed with water only, and extracted by shaking with an organic solvent. The further working-up is carried out in the usual manner.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating *Plasmodiophoromycetes, Oomycetes, Chytridiomycetes, Zygomycetes, Basidiomycetes* and *Deuteromycetes.*

The active compounds according to the invention have a broad spectrum of action and can be used against parasitic fungi which attack above-ground parts of plants or attack the plants through the soil, as well as against seed-borne pathogens.

They display a particularly good activity against parasitic fungi on above-ground parts of plants, such as species of *Erysiphe,* species of *Podosphaera* and species of *Venturia,* for example against the pathogen of apple mildew (*Podosphaera leucotricha*) and of apple scab (*Fusicladium dendriticum*). Furthermore, they display a high activity against cereal diseases, such as against cereal mildew.

An aspect to be singled out particularly is that the active compounds according to the invention not only display a protective action but are also systemically active. Thus, it proves possible to protect plants against fungal attack by supplying the active compound to the above-ground parts of the plant through the soil and the root or through the seed.

The compounds according to the invention have only a low toxicity to warm-blooded animals and, because of their low odor and their good toleration by human skin, they are not unpleasant to handle.

The active compounds according to the invention also engage in the metabolism of plants and can therefore be employed as plant growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production of the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the us of growth regulators. However, it is also possible to promote the shedding of fruit — for example in the case of table fruit — in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The active compounds according to the invention can be utilized, if desired, in the form of the usual informations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridge, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.). halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other fungicides and herbicides, or insecticides, acaricides, nematicides, bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compound concentrations in the use forms can be varied within a fairly wide range. They are, in general, from 0.1 to 0.00001 percent by weight, preferably from 0.05 to 0.0001%.

For the treatment of seed, amounts of active compound of 0.001 to 50 g, preferably 0.01 to 10 g, are generally employed per kilogram of seed.

In the case of their use as growth regulators, the concentrations of active compound can be varied within a fairly wide range. In general, concentrations of 0.00005 to 2%, preferably of 0.0001 to 0.5%, are used. Furthermore, in general 0.01 to 50 kg, preferably 0.05 to 10 kg, of active compound are employed per hectare of soil surface.

At higher use concentrations, the active compounds according to the invention also have a herbicidal action.

Furthermore, the present invention contemplates methods of selectively killing, combating or controlling fungi or plant growth, which comprises applying to at least one of correspondingly (a) such fungi, (b) such plants, and (c) the corresponding habitat thereof, i.e. the locus to be protected, e.g. to a growing crop, to an area where a crop is to be grown such as on or into the soil, to seed, or to a domestic animal, a correspondingly combative or toxic amount, i.e. a fungicidally or plant growth-regulating effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, foaming, gassing, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Fusicladium* test (apple)/Protective

Solvent: 4.7 parts by weight of acetone

Emulsifier: 0.3 part by weight of alkylaryl polyglycol ether

Water: 95 parts by weight.

The amount of active compound required for the desired concentration of the active compound in the spray liquid was mixed with the stated amount of solvent, and the concentrate was diluted with the stated amount of water which contained with stated additions.

Young apple seedlings in the 4–6 leaved stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse for 14 days.

15 days after inoculation, the infection of the seedlings was determined. The ratings obtained were converted to percent infection. 0% meant no infection; 100% meant that the plants were completely infected.

The active compounds, the concentrations of the active compounds and the results can be seen from the following table:

Table 1

| Active compound | Infection in % at an active compound concentration of 0.0025% |
|---|---|
| *Fusicladium* Test (apple) / protective | |
| 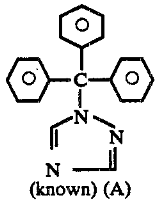 (known) (A) | 83 |
| 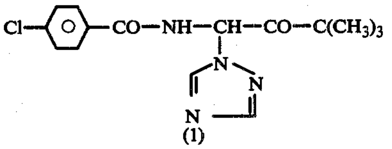 (1) | 50 |

Table 2

| Active compound | Infection in % at an active compound concentration of 0.00125% |
|---|---|
| *Podosphaera* Test (apple)/protective | |
| 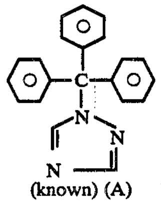 (known) (A) | 85 |
| 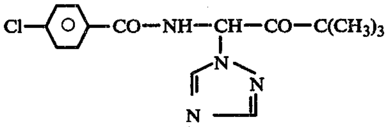 (1) | 50 |

EXAMPLE 2

*Podosphaera* test (apple)/protective

Solvent: 4.7 parts by weight of acetone

Emulsifier: 0.3 part by weight of alkylaryl polyglycol ether

Water: 95 parts by weight

The amount of active compound required for the desired concentration of the active compound in the spray liquid was mixed with the stated amount of solvent, and the concentrate was diluted with the stated amount of water which contained the stated additions.

Young apple seedlings in the 4–6 leaved stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21°–23° C. and at a relative atmospheric humidity of about 70%.

10 days after the inoculation, the infection of the seedlings was determined. The ratings obtained were converted to percent infection. 0% meant no infection: 100% meant that the plants were completely infected.

The active compounds, the concentrations of the active compounds and the results can be seen from the following table:

EXAMPLE 3

Shoot treatment test/powdery mildew of cereals/protective (leaf-destructive mycosis)

To produce a suitable preparation of active compound, 0.25 part by weight of active compound was taken up in 25 parts by weight of dimethylformamide and 0.06 part by weight of emulsifier alkylarylpolyglycol ether and then 975 parts by weight of water were added. The concentration was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei.*

After 6 days' dwell time of the plants at a temperature of 21°–22° C. and 80–90% atmospheric humidity the occurrence of mildew pustules on the plants was evaluated. The degree of infection was expressed as a percentage of the infection of the untreated control plants. 0% denoted no infection and 100% denoted that same degree of infection as in the case of the untreated control. The more active the compound, the lower was the degree of mildew infection.

The active compounds, the concentrations of the active compounds in the spray liquor and degrees of infection can be seen from the table which follows:

Table 3

| Active compounds | Active compound concentration in the spray liquor in % by weight | Infection in % of the untreated control |
|---|---|---|
| Shoot treatment test/powdery mildew of cereals/protective | | |
| untreated | — | 100.0 |
| 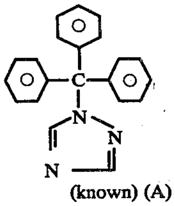 (known) (A) | 0.025<br>0.01 | 100.0<br>100.0 |

Table 3-continued
| Shoot treatment test/powdery mildew of cereals/protective | | |
|---|---|---|
| Active compounds | Active compound concentration in the spray liquor in % by weight | Infection in % of the untreated control |
| 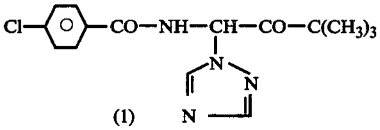 (1) | 0.01 | 0.0 |
| 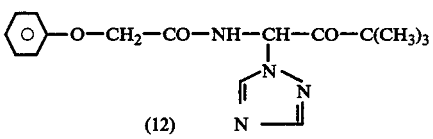 (12) | 0.01 | 32.5 |
| 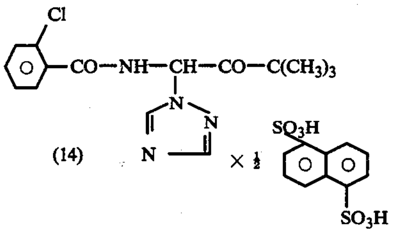 (14) | 0.025 | 50.0 |
| 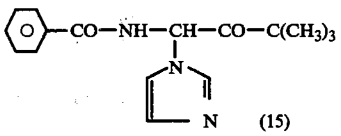 (15) | 0.025 | 12.5 |
| 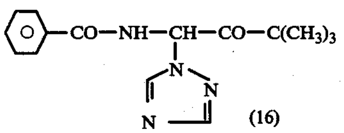 (16) | 0.025 | 500 |
| 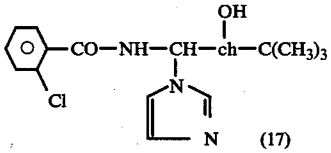 (17) | 0.025 | 28.8 |
| 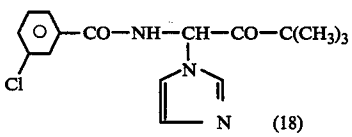 (18) | 0.025 | 28.8 |
| 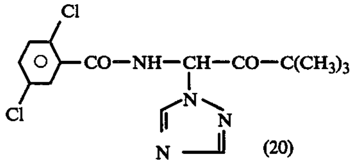 (20) | 0.025 | 50.0 |
| 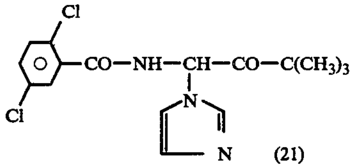 (21) | 0.025 | 21.3 |
| 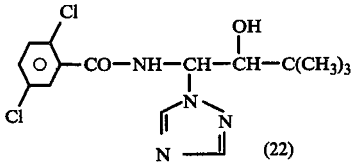 (22) | 0.025 | 40.0 |

Table 3-continued

Shoot treatment test/powdery mildew of cereals/protective

| Active compounds | Active compound concentration in the spray liquor in % by weight | Infection in % of the untreated control |
|---|---|---|
| 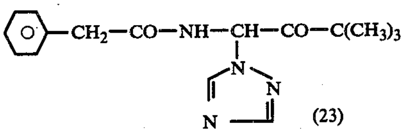 (23) | 0.025 | 40.0 |
| 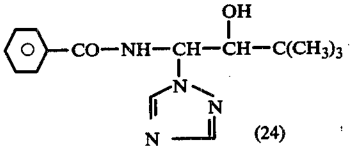 (24) | 0.025 | 40.0 |
| 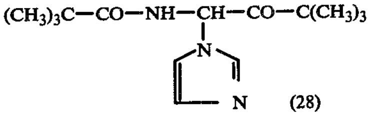 (28) | 0.025 | 30.0 |

EXAMPLE 4

Powdery mildew of barley (*Erysiphe graminis var. hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants have developed their first leaf, they were dusted with fresh spores of *Erysiphe graminis var. hordei* and grown on at 21°–22° C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

Table 4

Powdery mildew of barley test (*Erysiphe graminis var. hordei*)/systemic

| Active compound | Active compound concentration in the dressing in % by weight | Amount of dressing used in g/kg of seed | Infection in % of the untreated control |
|---|---|---|---|
| Without dressing | — | — | 100.0 |
| 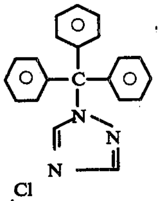 (known) (A) | 25 | 10 | 88.8 |
| 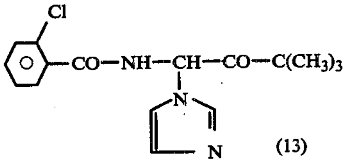 (13) | 25 | 10 | 55.0 |
| 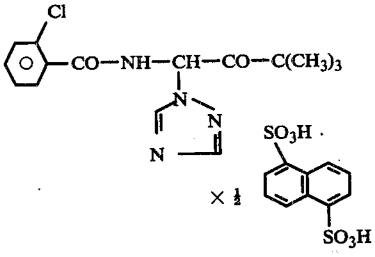 (14) | 25 | 10 | 0.0 |

Table 4-continued

| Powdery mildew of barley test (*Erysiphe graminis var. hordei*)/systemic | | | |
|---|---|---|---|
| Active compound | Active compound concentration in the dressing in % by weight | Amount of dressing used in g/kg of seed | Infection in % of the untreated control |
| 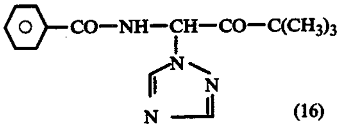 (16) | 25 | 10 | 0.0 |
| 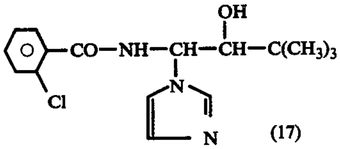 (17) | 25 | 10 | 58.8 |
| 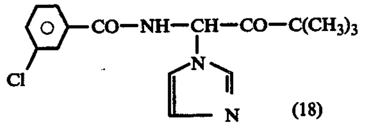 (18) | 25 | 10 | 50.0 |
| 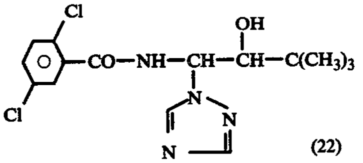 (22) | 25 | 10 | 25.0 |
| 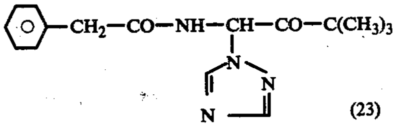 (23) | 25 | 10 | 0.0 |
| 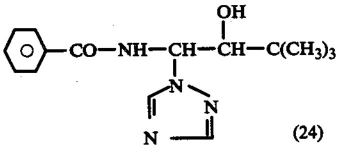 (24) | 25 | 10 | 17.5 |
| 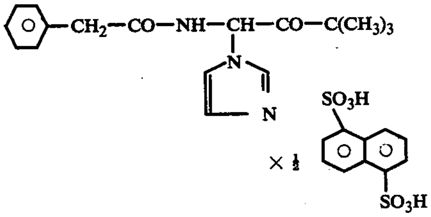 (25) | 25 | 10 | 50.0 |
| 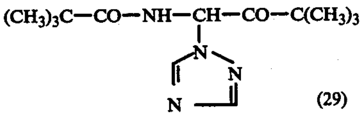 (29) | 25 | 10 | 25.0 |

EXAMPLE 5

Influence on growth/soya beans

Solvent: 10 parts by weight of methanol

Emulsifier: 2 parts by weight of polyoxyethylene sorbitan monolaurate

To prepare a suitable preparation of active compound, 1 part by weight of active compound was mixed with the stated amounts of solvent and emulsifier and the mixture was made up to the desired concentration with water.

Young soya bean plants, in the stage in which the first secondary leaves had unfolded, were sprayed with the preparation of active compound until dripping wet. After 3 weeks, the additional growth was measured and the inhibition of growth in % of the additional growth of the control plants was calculated. 0% denoted growth corresponding to that of the control plants. Positive values characterized promotion of growth compared to the control plants while negative values corrrespondingly indicated an inhibition of growth.

The active compounds, concentrations of the active compounds and results can be seen from the table which follows:

Table 5

| Influence on growth/soya beans | | |
|---|---|---|
| Active compound | Concentration in % | Influence on growth in % |
| control | — | = 0 |
| 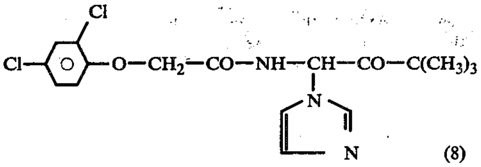 (8) | 0.05 | − 85* |
| 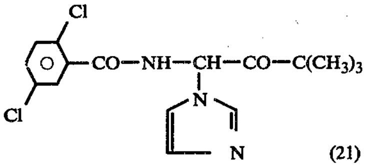 (21) | 0.05 | + 30 |
| 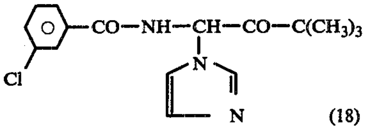 (18) | 0.05 | + 20 |

NOTE:
*dark green leaves

EXAMPLE 6

Inhibition of growth/barley

Solvent: 10 parts by weight of methanol
Emulsifier: 2 parts by weight of polyoxyethylene sorbitan monolaurate To prepare a suitable preparation of active compound, 1 part by weight of active compound was mixed with the stated amount of solvent and emulsifier and the mixture was made up to the desired concentration with water.

Young barley plants, in the 2-leaf stage, were sprayed with the preparation of active compound until dripping wet. After the untreated control plants had reached a growth height of about 60 cm, the additional growth of all the plants was measured and the inhibition of growth in % of the additional growth of the control plants was calculated. 100% meant that growth had stopped and 0% denoted a growth corresponding to that of the untreated control plants.

The active compounds, concentrations of the active compounds and results can be seen from the table which follows.

Table 6

| Inhibition of growth/barley | | |
|---|---|---|
| Active compound | Concentration in % | Inhibition of growth in % |
| control | — | = 0 |
| 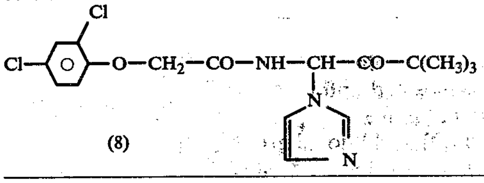 (8) | 0.05 | 45 |

EXAMPLE 7

Inhibition of the growth of side shoots of tobacco

Solvent: 10 parts by weight of methanol
Emulsifier: 2 parts by weight of polyoxyethylene-sorbitan monolaurate To prepare a suitable preparation of active compound, 1 parts by weight of active compound was mixed with the stated amounts of solvent and emulsifier and the mixture was made up to the desired concentration with water.

The shoot tips of about 50 cm high tobacco plants were broken off. On the following day, the plants were sprayed with the preparations of active compound until dripping wet. After 3 weeks, the side shoots which had formed during this time were broken off. All the side shoots of one treatment were weighed. The weight of the side shoots of the treated plants was compared with the weight of the side shoots of the untreated control plant. 100% inhibition denoted the absence of side shoots and 0% denoted a growth of side shoots which correspond to that of the control plants.

The active compounds, the concentrations of the active compounds and results can be seen from the table which follows:

Table 7

| Inhibition of the growth of side shoots of tobacco | | |
|---|---|---|
| Active compound | Concentration in % | Inhibition in % |
| Control | — | = 0 |

Table 7-continued

| Active compound | Inhibition of the growth of side shoots of tobacco — Concentration in % | Inhibition in % |
|---|---|---|
| Off-Shoot-T* | 0.2 | 20 |
| 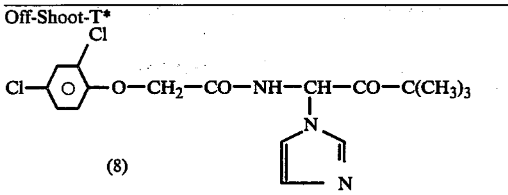 (8) | 0.2 | 97 |

*NOTE:
Off-Shoot-T is a commercial product based on fatty alcohols. It consists of 0.5% of $C_6$-alcohols, 42% of $C_8$-alcohols, 56% of $C_{10}$-alcohols and 1.5% of $C_{12}$-alcohols and thus principally consists of octanol and decanol.

The process of this invention is illustrated by the following preparative examples:

EXAMPLE 8

(a) Preparation of the precursor

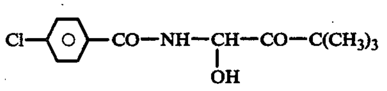

14 g (0.123 mol) of freshly distilled tert.-butylglyoxal were dissolved in 150 ml of absolute benzene. 19.1 g (0.123 mol) of p-chlorobenzamide were added and the mixture was heated for 15 hours under reflux. On cooling, the reaction product crystallised out. 16.1 g (54% of theory) of 1-(p-chlorobenzamido)-3,3-dimethyl-1-hydroxy-butan-2-one of melting point 130° C. were obtained.

(b) Preparation of the intermediate

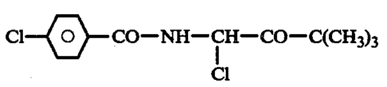

12.1 g (0.05 mol) of 1-(p-chlorobenzamido)-3,3-dimethyl-1-hydroxy-butan-2-one were dissolved in 80 ml. of carbon tetrachloride. 10.4 g (0.05 mol) of phosphorus pentachloride were added at 50° C. and the mixture was then heated for 2 hours under reflux. It was then filtered hot and the filtrate was concentrated in a waterpump vacuum. The crude 1-chloro-1-(p-chlorobenzamido)-3,3-dimethyl-butan-2-one thus obtained could be directly reacted further. The melting point was 132°-135° C.

c)

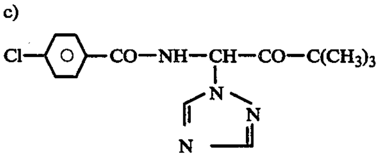

(1)

Process variant (a)

A solution of 269.5 g (1 mol) of 1-chloro-1-(p-chlorobenzamido)-3,3-dimethyl-butan-2-one in 1,000 ml of absolute tetrahydrofuran was added dropwise, in the course of 30 minutes, to a suspension of 150 g (2.1 mol) of 1,2,4-triazole and 140 ml (1 mol) of triethylamine in 1,000 ml of absolute tetrahydrofuran in the temperature range from 20° to 40° C., with slight cooling. The mixture was stirred for 15 hours at room temperature and was then concentrated in a waterpump vacuum. The reaction mixture was then extracted with methylene chloride/water and the organic phase was separated off and dried over sodium sulphate. It was concentrated by distilling off the solvent in vacuo, the residue was dissolved in 1,000 ml of ethyl acetate and 36 g (1 mol) of hydrogen chloride were passed in. The precipitate was filtered off, washed with a little ethyl acetate, suspended in methylene chloride and neutralized with saturated aqueous sodium bicarbonate solution. The organic phase was separated off, washed with water, dried over sodium sulphate and concentrated. After recrystallization from ethyl acetate, 145 g (45% of theory) of 1-(p-chlorobenzamido)-3,3-dimethyl-1-(1,2,4-triazol-1-yl) butan-2-one of melting point 160° C. were obtained.

EXAMPLE 9

(a) Preparation of the precursor

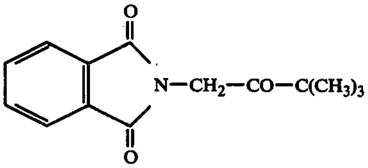

37 g (0.2 mol) of potassium phthalimide were suspended in 200 ml of acetone. 26.9 g (0.2 mol) of α-chloropinacoline were added dropwise at the boil. The mixture was heated for 10 hours under reflux and was then filtered in the cold, and the residue was washed with acetone. The filtrate was concentrated by distilling off the solvent. The residue was recrystallized from cyclohexane. 23.8 g (45% of theory) of phthalimidopinacoline of melting point 93°-96° C. were obtained.

(b) Preparation of the intermediate

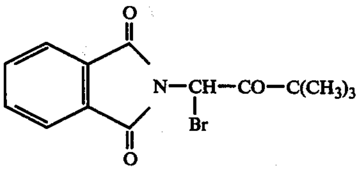

76.8 g (0.314 mol) of phthalimidopinacoline were dissolved in 100 ml of carbon tetrachloride and 200 ml of methylene chloride. 16 ml (0.314 mol) of bromine in 50 ml of carbon tetrachloride were added dropwise, at 60° C. at a rate such that steady consumption occurred. The solvent was then distilled off in vacuo. The crude 1-bromo-3,3-dimethyl-1-phthalimido-butan-2-one which remained was reacted further without isolation.

It could also be caused to crystallize by adding petroleum ether. The melting point was 86°-94° C.

c)

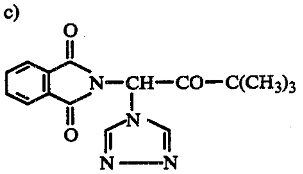

(2)

Process variant (a)

21 g (0.3 mol) of 1,2,4-triazole were added to 32.4 g (0.1 mol) of 1-bromo-3,3-dimethyl-1-phthalimido-butan-2-one in 200 ml of acetontrile. The mixture was heated for 24 hours under reflux and was then concentrated in a waterpump vacuum. The residue was taken up in 200 ml of methylene chloride and the solution was washed three times in 100 ml of water at a time, dried over sodium sulphate and concentrated in vacuo by distilling off the solvent. The residue was taken up in 200 ml of acetone, the solution was heated with active charcoal and filtered, and 18 g of 1,5-naphthalenedisulphonic acid were added to the filtrate. The resulting precipitate (25.4 g of the naphthalenedisulphonate salt of melting point 155°-162° C., with decomposition) was neutralized with sodium hydrogen carbonate solution. The oil thereby formed was recrystallized from petroleum ether/ethanol. 7.3 g (23% of theory) of 3,3-dimethyl-1-phthalimido-1-(1,2,4-triazol-4-yl)-butan-2-one of melting point 189°-196° C. were obtained.

EXAMPLE 10

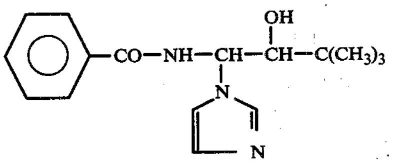

(3)

Process variant (b) 28.5 g (0.1 mol) of 1-benzamido-3,3-dimethyl-1-(imidazol-1-yl)-butan-2-one of melting point 140°-142° C. (prepared analogously to Example 8, in accordance with process (a)) were dissolved in 250 ml of methanol. 4 g (0.1 mol) of sodium borohydride were added in portions while stirring and cooling at 0° to 10° C. Stirring was continued for 15 hours at room temperature and 200 ml of water were added to the reaction mixture. The mixture was then extracted by shaking with 200 ml of methylene chloride and the organic phase as dried over sodium sulphate and concentrated by distilling off the solvent in vacuo. Boiling up with petroleum ether and a little ether caused the mixture to crystallize. 22.6 g (79% of theory) of 1-benzamido-3,3-dimethyl-1-imidazol-1-yl-butan-2-ol of melting point 143° C. were obtained.

EXAMPLE 11

(4)

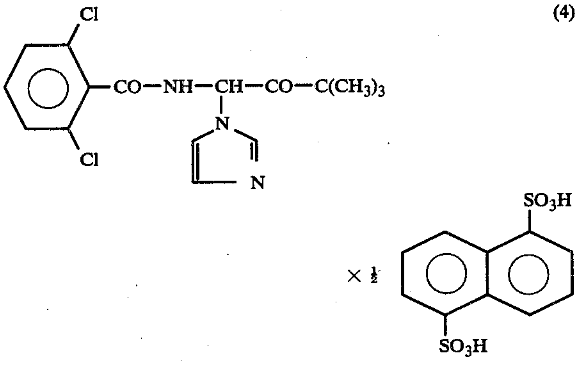

Salt formation 152 g (0.5 mol) of 1-chloro-1-(2,6-dichlorobenzamido)-3,3-dimethyl-butan-2-one in 300 ml of tetrahydrofuran were added dropwise in the course of one hour at 10° C., to a suspension of 70 g (1.1 mol) of imidazole and 70 ml (0.5 mol) of triethylamine in 300 ml of tetrahydrofuran. The mixture was stirred for 15 hours at room temperature and filtered, and the residue was rinsed with ethyl acetate. The filtrate was concentrated in a waterpump vacuum and the residue was taken up in 500 ml of methylene chloride and washed three times with 200 ml water at a time. After drying over sodium sulphate, the solvent was distilled off in a waterpump vacuum. The oil which remained was dissolved in 500 ml of acetone and 90 g (0.3 mol) of 1,5-naphthalenedisulphonic acid in acetone were added. The crystals which precipitated were filtered off and washed with acetone/water (10:1). 14.9 g (21.8% of theory) of 1-(2,6-dichlorobenzamido)-3,3-dimethylbutan-1-(imidazol-1-yl)-butan-2-one-naphthalene-1,5-disulphonate of melting point 220°-230° C. (decomposition) were obtained.

The examples in the table which follows were obtained by methods analogous to those described in Example 8-11.

Table 8

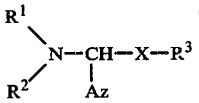

(I)

| Compound No. | $R^1$ | $R^2$ | $R^3$ | X | Az | Melting point (° C) |
|---|---|---|---|---|---|---|
| 5 | 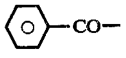 | H | 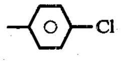 | CO | 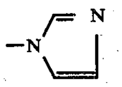 | 212 |
| 6 | 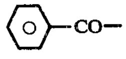 | H | 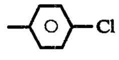 | CH(OH) | 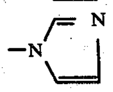 | 185-87 |
| 7 | $CH_3$—CO— | H | 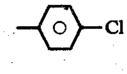 | CO | 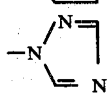 | 199-203 |

Table 8-continued
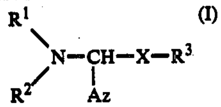
(I)
| Compound No. | $R^1$ | $R^2$ | $R^3$ | X | Az | Melting point (° C) |
|---|---|---|---|---|---|---|
| 8 | 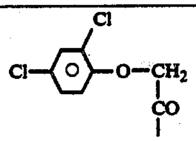 | H | $C(CH_3)_3$ | CO | 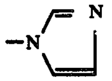 | 130–35 |
| 9 | $CCl_3$—CO— | H | $C(CH_3)_3$ | CO | 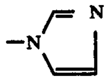 | 150–55 |
| 10 | 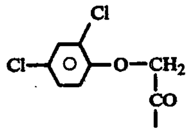 | H | $C(CH_3)_3$ | CH(OH) | 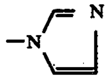 | 180 |
| 11 | 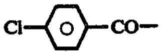 | H | $C(CH_3)_3$ | CO | 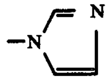 | 227–30 (× HCl) |
| 12 | 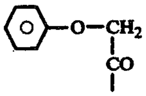 | H | $C(CH_3)_3$ | CO | 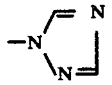 | 170 |
| 13 | 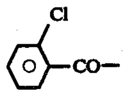 | H | $C(CH_3)_3$ | CO | 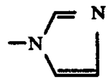 | 143–45 |
| 14 | 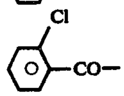 | H | $C(CH_3)_3$ | CO | 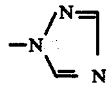 | 220–25 (X ½ 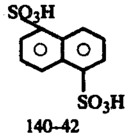 ) |
| 15 | 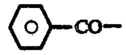 | H | $C(CH_3)_3$ | CO | 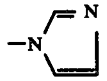 | 140–42 |
| 16 | 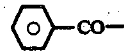 | H | $C(CH_3)_3$ | CO | 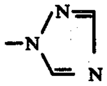 | 130–36 |
| 17 | 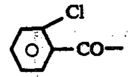 | H | $C(CH_3)_3$ | CH(OH) | 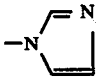 | 117–19 |
| 18 | 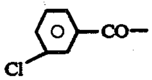 | H | $C(CH_3)_3$ | CO | 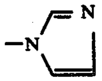 | 129–32 (decomposition) |
| 19 | 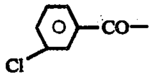 | H | $C(CH_3)_3$ | CO | 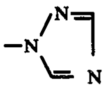 | 94–97 |
| 20 | 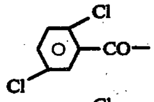 | H | $C(CH_3)_3$ | CO | 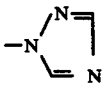 | 119–20 |
| 21 | 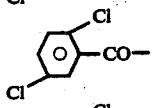 | H | $C(CH_3)_3$ | CO | 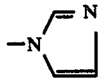 | 164–65 |
| 22 | 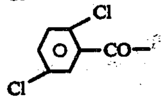 | H | $C(CH_3)_3$ | CH(OH) | 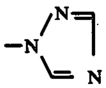 | 152–53 |

Table 8-continued

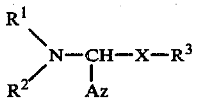 (I)

| Compound No. | $R^1$ | $R^2$ | $R^3$ | X | Az | Melting point (° C) |
|---|---|---|---|---|---|---|
| 23 | 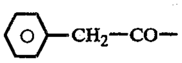 | H | $C(CH_3)_3$ | CO | 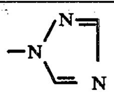 | 129-30 |
| 24 | 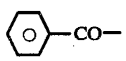 | H | $C(CH_3)_3$ | CH(OH) | 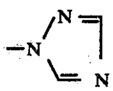 | 143 (decomposition) |
| 25 | 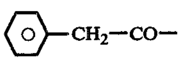 | H | $C(CH_3)_3$ | CO | 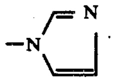 | 212 (decomposition) (X ½ 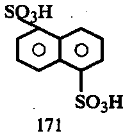 ) |
| 26 | 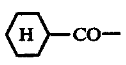 | H | $C(CH_3)_3$ | CO | 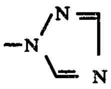 | 171 |
| 27 | 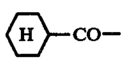 | H | $C(CH_3)_3$ | CO | 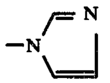 | 164-65 |
| 28 | $(CH_3)_3C—CO—$ | H | $C(CH_3)_3$ | CO | 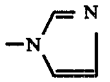 | 173 |
| 29 | $(CH_3)_3C—CO—$ | H | $C(CH_3)_3$ | CO | 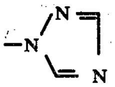 | 104-05 |
| 30 | 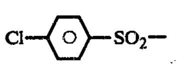 | H | $C(CH_3)_3$ | CO | 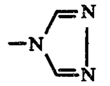 | 185-89 |
| 31 | 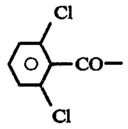 | H | $C(CH_3)_3$ | CO | 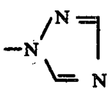 | 180-84 |

The methanesulfonic acid amide counterpart of compound 30 can be similarly prepared as can other amides.

It will be appreciated that the instant specification and examples are set forth by way of illustration and not limitation, and that various modifications and changes may be made without departing from the spirit and scope of the present invention.

What is claimed is:

1. A 1-amido-1-azolyl-2-hydroxy- or -keto-alkane of the formula

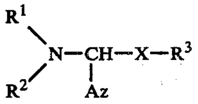

in which X is

 or , $R^1$ is phenyl, phenyl substituted by at least one halogen or alkyl with 1 or 2 carbon atoms, $R^4$—$SO_2$— or $R^5$—CO—, $R^2$ is hydrogen, or $R^1$ and $R^2$ conjointly with the linking nitrogen atom are phthalimide, $R^3$ is alkyl with 1 to 4 carbon atoms, phenyl, or phenyl substituted by at least one halogen or alkyl with 1 or 2 carbon atoms, $R^4$ is alkyl with 1 to 4 carbon atoms, halogenoalkyl with up to 2 carbon atoms and up to 5 halogen atoms, cycloalkyl with 5 to 7 carbon atoms optionally substituted by alkyl with 1 or 2 carbon atoms, or aryl, aralkyl or aryloxyalkyl each with 6 to 10 carbon atoms in the aryl part and the last two each having up to 4 carbon atoms in the alkyl part, which alkyl part is optionally substituted by halogen whereas the aryl part of these three radicals optionally carries a substituent selected from the group consisting of halogen, alkyl with 1 to 4 carbon atoms, halogenoalkyl with up to 2 carbon atoms and up to 4 halogen atoms, methoxy, ethoxy, methylthio, ethylthio, nitro, cyano, phenyl, halophenyl, phenoxy and halophenoxy, $R^5$ is alkyl with 1 to 4 carbon atoms, and Az is imidazol-1-yl, 1,2,4-triazol-1-yl, 1,2,4-triazol-4-yl or 1,2,3-triazol-1-yl or a physiologically tolerated salt thereof.

2. The compound according to claim 1 wherein such compound is 1-(p-chorobenzamido)-3,3-dimethyl-1-(1,2,4-triazol-1-yl)-butan-2-one of the formula

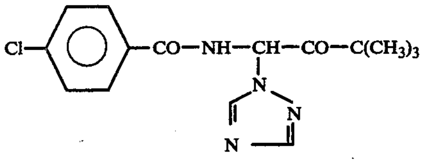

or a physiologically tolerated salt thereof.

3. The compound according to claim 1 wherein such compound is 1-(2,4-dichlorophenoxyacetamido)-3,3-dimethyl-1(imidazol-1-yl)-butan 2-one of the formula

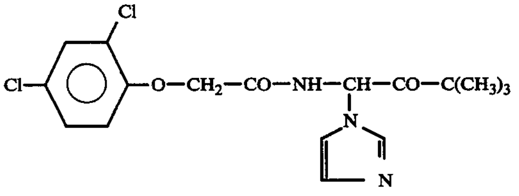

or a physiologically tolerated salt thereof.

4. The compound according to claim 1 wherein such compound is 1-benzamido-3,3-dimethyl-1-(1,2,4-triazol-1-yl)-butan-2-one of the formula

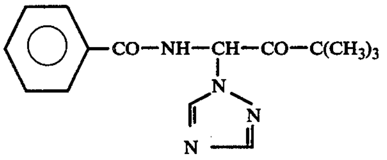

or a physiologically tolerated salt thereof.

5. The compound according to claim 1 wherein such compound is 1-phenylacetamido-3,3-dimethyl-1-(1,2,4-triazol-1-yl)-butan-2-one of the formula

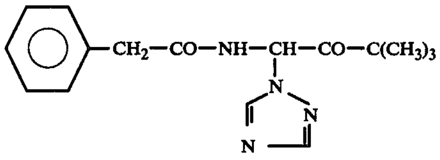

or a physiologically tolerated salt thereof.

6. A fungicidal or plant growth-regulating composition containing as active ingredient a fungicidally or plant growth-regulating effective amount of a compound according to claim 1 in admixture with a dilutent.

7. A method of combating fungi or regulating the growth of plants which comprises applying to the fungi, to the plants, or to a habitat thereof, a fungicidally or plant growth-regulating effective amount of a compound according to claim 1.

8. The method according to claim 7, in which said compound is 1-(p-chlorobenzamido)-3,3-dimethyl-1-(1,2,4-triazol-1-yl)-butan-2-one, 1-(2,4-dichlorophenoxyacetamido)-3,3-dimethyl-1-(imidazol-1-yl)-butan-2-one, 1-benzamido-3,3-dimethyl-1-(1,2,4-triazol-1-yl)-butan-2-one, or 1-phenylacetamido-3,3-dimethyl-1-(1,2,4-triazol-1-yl)-butan-2-one, or a physiologically tolereated salt thereof.

9. The method according to claim 7 wherein the compound is applied to a plant or plant habitat to regulate the growth of the plant.

* * * * *